US008941758B2

(12) United States Patent
Yamada

(10) Patent No.: US 8,941,758 B2
(45) Date of Patent: Jan. 27, 2015

(54) IMAGE PROCESSING APPARATUS AND IMAGE PROCESSING METHOD FOR GENERATING A COMBINED IMAGE

(75) Inventor: Naoki Yamada, Soka (JP)

(73) Assignee: Canon Kabushiki Kaisha, Tokyo (JP)

( * ) Notice: Subject to any disclaimer, the term of this patent is extended or adjusted under 35 U.S.C. 154(b) by 381 days.

(21) Appl. No.: 13/215,940

(22) Filed: Aug. 23, 2011

(65) Prior Publication Data

US 2012/0050576 A1   Mar. 1, 2012

(30) Foreign Application Priority Data

Aug. 31, 2010 (JP) ................................. 2010-194466

(51) Int. Cl.
| | | |
|---|---|---|
| H04N 5/262 | (2006.01) | |
| H05G 1/64 | (2006.01) | |
| G03B 42/02 | (2006.01) | |
| G03B 42/08 | (2006.01) | |
| A61B 6/00 | (2006.01) | |
| H04N 5/32 | (2006.01) | |

(52) U.S. Cl.
CPC ................ *G03B 42/02* (2013.01); *G03B 42/08* (2013.01); *A61B 6/5235* (2013.01); *H04N 5/32* (2013.01)

USPC ........................................ 348/239; 378/98.12

(58) Field of Classification Search
USPC ......... 348/239; 396/287; 382/132; 378/98.12
See application file for complete search history.

(56) References Cited

U.S. PATENT DOCUMENTS

| | | | | |
|---|---|---|---|---|
| 2007/0025723 | A1* | 2/2007 | Baudisch et al. | 396/287 |
| 2007/0140427 | A1* | 6/2007 | Jensen et al. | 378/98.12 |
| 2010/0149368 | A1* | 6/2010 | Yamashita et al. | 348/222.1 |

FOREIGN PATENT DOCUMENTS

JP      3679647 B     8/2005

* cited by examiner

*Primary Examiner* — Twyler Haskins
*Assistant Examiner* — Quang Le
(74) *Attorney, Agent, or Firm* — Canon USA Inc. IP Division

(57) ABSTRACT

An image processing apparatus is configured to generate a combined image by combining a plurality of photographed images. The image processing apparatus includes an acquisition unit configured to acquire the plurality of photographed images from a photographing unit, and a setting unit configured to designate, if misshooting or reshooting of a first photographed image of the plurality of photographed images is designated, misshooting or reshooting of a second photographed image of the plurality of photographed images.

12 Claims, 11 Drawing Sheets

FIG. 5
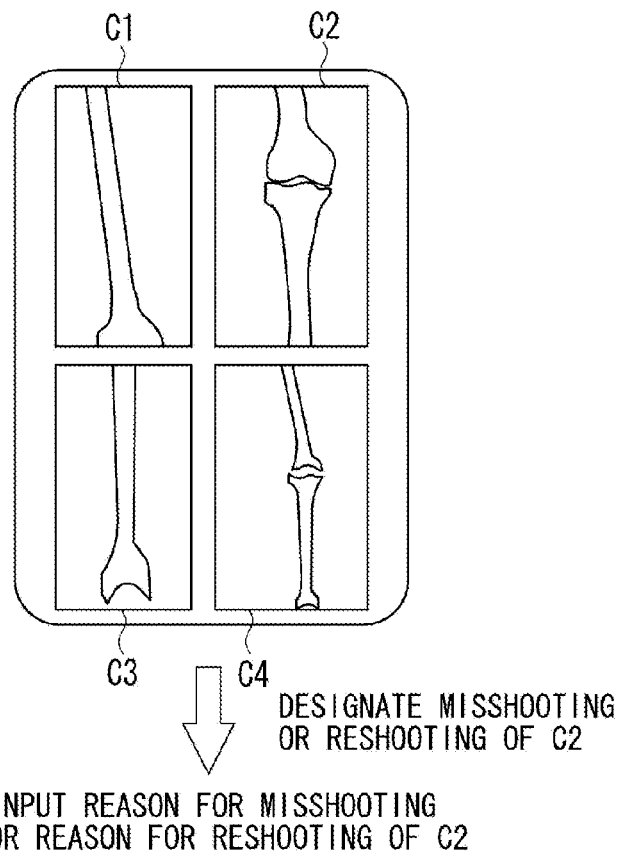
DESIGNATE MISSHOOTING OR RESHOOTING OF C2
INPUT REASON FOR MISSHOOTING OR REASON FOR RESHOOTING OF C2
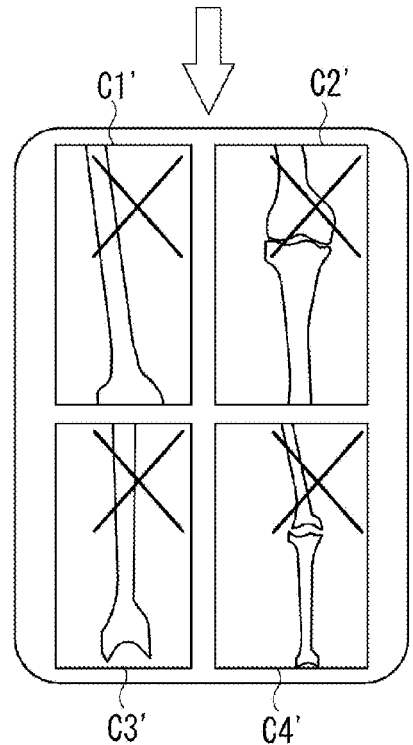

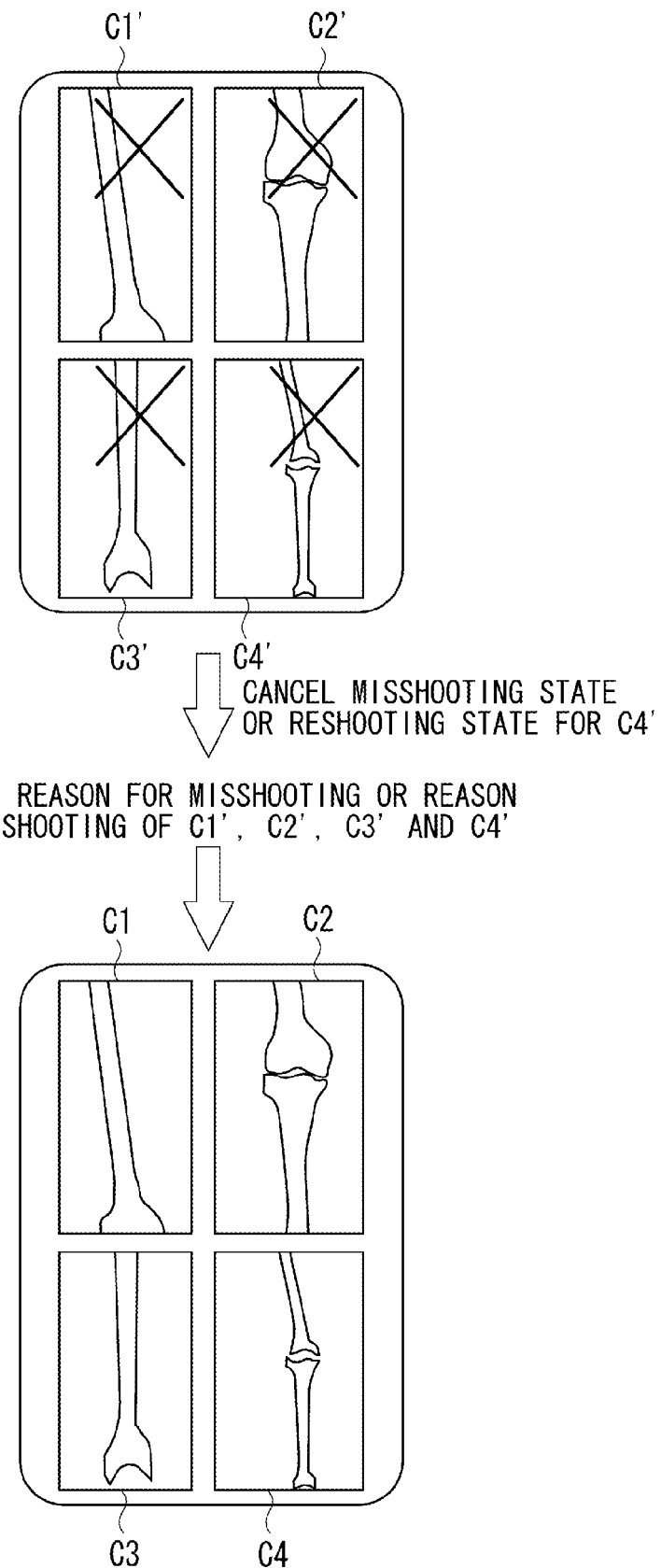

IMAGE PROCESSING APPARATUS AND IMAGE PROCESSING METHOD FOR GENERATING A COMBINED IMAGE

BACKGROUND OF THE INVENTION

1. Field of the Invention

The present invention relates to an image processing apparatus and a method for generating a combined image by combining a plurality of photographed images.

2. Description of the Related Art

Conventionally, radiographic imaging has been successfully used in various fields. Particularly in medical fields, the photographing using radiation is one of the most important methods for diagnosis. In recent years, an image sensor for collecting radiation images obtained by radiography as digitized image data has been put into practical use. Digitalization has progressed in the field of radiography. Generally, mainstream large-sized image sensors have a size of 43 centimeters (cm) by 43 cm.

If radiography is to be performed on a region (e.g., the whole spine or the full lower leg of a subject) larger than the image sensor, the entire region cannot be photographed by a single time of shooting (single shot). Accordingly, the object is photographed by taking a plurality of partial images thereof at a plurality of times of shooting (multiple shots), respectively. Indeed, a shooting method has been established, in which large image data representing a desired single image of the entire object is obtained by combining a plurality of pieces of image data, which are respectively acquired at the plurality of times of shooting. Generally, such a shooting method is called a divisional shooting method, a long-size shooting method, a stitch shooting method, or the like (hereinafter, such a shooting method is generally referred to as a stitch shooting method).

In the radiography in the medical field, misshooting or reshooting is designated with respect to a photographed image in view of a case where a patient moves when an image thereof is photographed. In some countries and regions, it is obligated to retain, at that time, a reason for misshooting or reshooting as a record.

Japanese Patent No. 3679647 discusses the above misshooting or reshooting. Hereinafter, a conventional method for designating the misshooting or reshooting is described with reference to FIGS. 9A and 9B. As illustrated in FIGS. 9A and 9B, a combined image C4 is obtained by combining three photographed images C1, C2, and C3 that are acquired by being shot according to the stitch shooting method.

As illustrated in FIG. 9A, if an operator designates, upon completion of shooting of a second photographed image C2, misshooting or reshooting of the image C2, then, the operator inputs, to an image processing apparatus, a reason for misshooting or reshooting of the second photographed image C2. Upon completion of inputting the reason, a cross mark is displayed on the second photographed image C2. Thus, the second photographed image C2 is changed to an image C2'. Consequently, it is confirmed that the misshooting or reshooting of the image C2 is designated.

As illustrated in FIG. 9B, if a desired image is not obtained as a combined image C4 that is formed upon completion of shooting of three images C1, C2, and C3, the operator designates misshooting or reshooting of the combined image C4. If the operator designates the misshooting or reshooting of the combined image C4 similarly to the designation of the misshooting or reshooting of the image C2 illustrated in FIG. 9A, then, the operator inputs, to the image processing apparatus, a reason for misshooting or reshooting of the combined image C4. Upon completion of inputting the reason, a cross mark is displayed on the combined image C4. Thus, the combined image C4 is changed to an image C4'. Consequently, it is confirmed that the misshooting or reshooting of the combined image C4 is designated.

According to the method of the designation of misshooting or reshooting illustrated in FIGS. 9A and 9B, the designation of misshooting or reshooting is performed on a single photographed-image or combined-image. However, sometimes, such a method of the designation of misshooting or reshooting is not effective in the case of employing the stitch shooting method aimed at forming a combined image, for the following reason.

According to the stitch shooting method, even if the reshooting of the second photographed image C2 is designated as illustrated in FIG. 9A, and then performed, there is little possibility that a reshot image obtained by the reshooting of the image C2 is incorrectly combined with the first photographed image C1. This is caused by, e.g., the fact that the patient moves while the second image is reshot.

Accordingly, the designation of misshooting or reshooting of the photographed image C2 means that both of the first and second images C1 and C2 are reshot. Thus, if the misshooting or reshooting of the second photographed image C2 is designated, the misshooting or reshooting of the first photographed image C1 should also be designated.

On the other hand, if a combined image is reformed by designating the misshooting or reshooting of the combined image C4, the images C1, C2, and C3 photographed to form the combined image C4 are unnecessary. Accordingly, if the misshooting or reshooting of the combined image C4 is designated, the misshooting or reshooting of each of the photographed images C1, C2, and C3 should also be designated.

Thus, according to the conventional method of the designation of misshooting or reshooting, the designation of misshooting or reshooting of an image shot according to the stitch shooting method is not taken into consideration. For example, if the misshooting of all of the images C1 through C4 illustrated in FIG. 9B is designated, each of the designation of the misshooting and the input of the reason for the misshooting should be performed four times. Thus, the conventional method is cumbersome for operators. In addition, there is possibility that unnecessary photographed images are transferred and printed due to an operator's carelessness of the designation of misshooting.

SUMMARY OF THE INVENTION

The present invention is directed to a reduction of burden concerning the designation of misshooting or reshooting, which is imposed on an operator in an image processing apparatus for generating a combined image by combining a plurality of photographed images.

According to an aspect of the present invention, an image processing apparatus for generating a combined image by combining a plurality of photographed images includes an acquisition unit configured to acquired the plurality of photographed images from a photographing unit, and a setting unit configured to designate, if misshooting or reshooting of a first photographed image of the plurality of photographed images is designated, misshooting or reshooting of a second photographed image of the plurality of photographed images.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 5 illustrates a process in the case of designation of misshooting or reshooting of a combined image.

FIG. 8 illustrates another process in the case of cancelling the designation of misshooting or reshooting.

DESCRIPTION OF THE EMBODIMENTS

Various exemplary embodiments, features, and aspects of the invention will be described in detail below with reference to the drawings.

Figure 1:
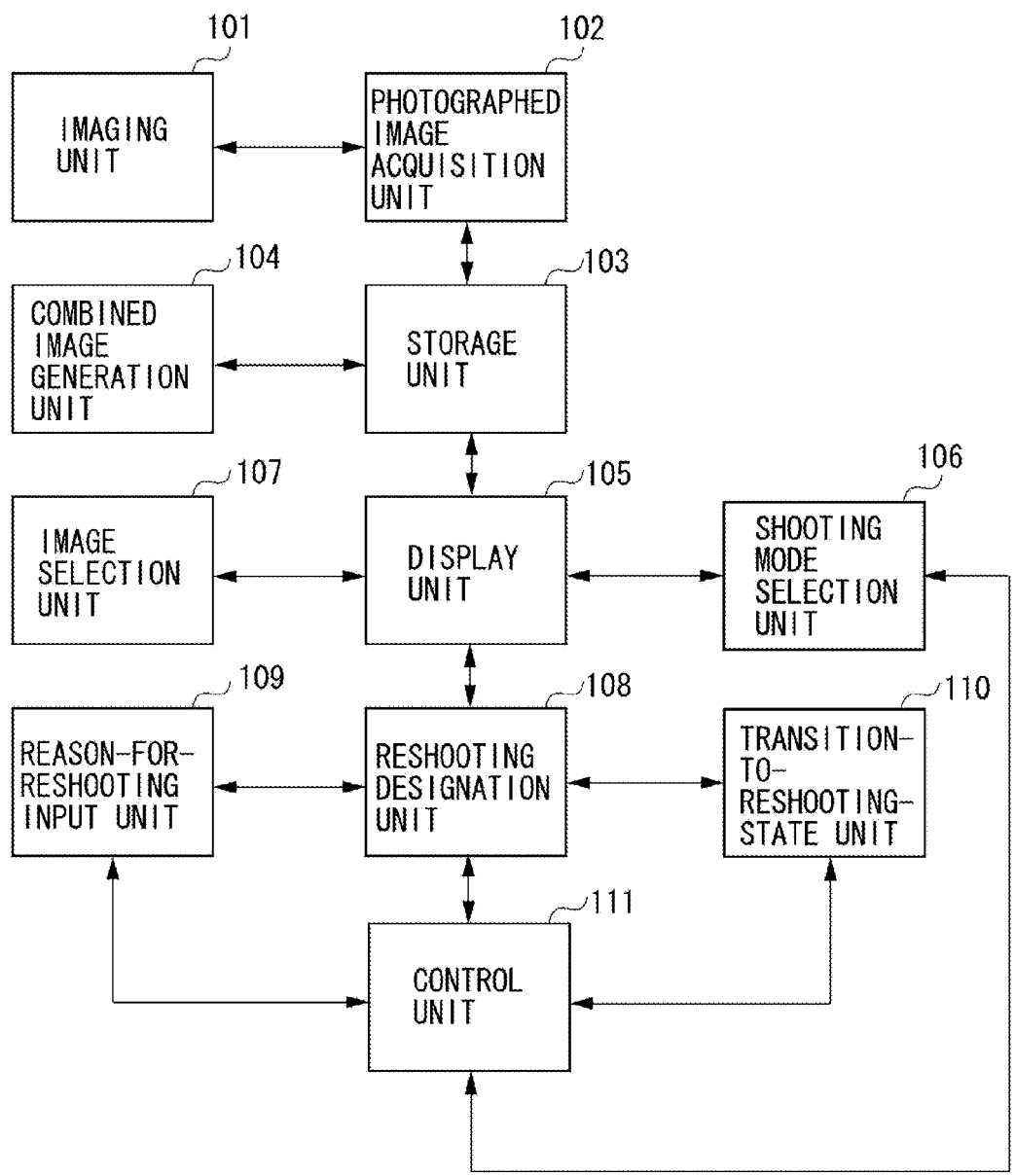
FIG. 1 illustrates a configuration of an image processing apparatus according to an exemplary embodiment of the present invention.

FIG. 1 illustrates a configuration of an image processing apparatus according to an exemplary embodiment of the present invention. An imaging unit 101 acquires an X-ray photographed image (or a radiographic image) by detecting X-rays (or radiation) passing through an object. The imaging unit 101 functions as an X-ray detection unit (or a radiographing unit) that detects X-rays (or radiation). The imaging unit 101 is configured to include a photoelectric conversion element or the like, which can detect X-rays (or radiation).

A photographed image acquisition unit 102 functions as an acquisition unit that acquires an X-ray photographed image obtained by the imaging unit 101. A storage unit 103 stores X-ray photographed images acquired by the photographed image acquisition unit 102. The storage unit 103 is configured by a temporary storage unit such as a random access memory (RAM), a storage unit such as a hard disk drive (HDD), or the like.

A combined image generation unit 104 functions as a unit for generating a combined image from at least two (i.e., a first photographed image and a second photographed image) photographed images stored in the storage unit 103. Generally, the combined image generation unit 104 performs digital processing on digital data representing X-ray photographed images. Thus, the combined image generation unit 104 has a configuration similar to that of a personal computer having a central processing unit (CPU) such as a microprocessor, a RAM, and the like. The combined image generation unit 104 has a storage medium that stores a computer program for combining photographed images, and for performing other functions.

The storage unit 103 can also store a combined image generated by the combined image generation unit 104.

A display unit 105 displays the photographed images and the combined image stored in the storage unit 103. The display unit 105 is configured by a monitor for displaying general images, and the like. A shooting mode selection unit 106 selects a shooting mode by receiving a designation from an operator who operates the imaged processing apparatus according to the present exemplary embodiment. The selection of the shooting mode is performed while the operator confirms a graphical user interface (GUI) displayed on the display unit 105. The selectable shooting modes includes an ordinary shooting mode in which only a single image of a chest region or the like is shot, and a stitch shooting mode in which stitch shooting is performed. As described above, the stitch shooting mode is a shooting mode in which a plurality of photographed images are connected (or combined) to generate a combined image.

Figure 2:
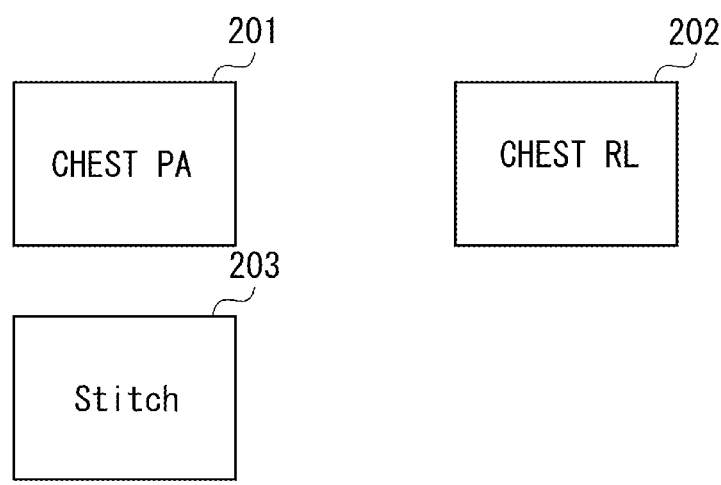
FIG. 2 illustrates an example of selection of a shooting mode by a shooting mode selection unit.

FIG. 2 illustrates an example of selection of a shooting mode by the shooting mode selection unit 106. FIG. 2 also illustrates an example of the GUI displayed on the display unit 105. In FIG. 2, a button 201, on which the name "CHEST PA" is written, and another button 202, on which the name "CHEST RL" is written, are those for ordinary shooting modes. The operator can select the ordinary shooting mode by pressing the button 201 or 202. On the other hand, a button 203, on which the name "Stitch" is written, is that for the stitch shooting mode. The operator can select the stitch shooting mode by pressing the button 203. In FIG. 2, the buttons 201, 202 and 203 may be implemented as physical hardware units (e.g., as pushbuttons connected to circuits), or these may be implemented as interactive software modules (e.g., as interactive icons in a touch-screen interface), or a combination of software/hardware elements.

Returning to FIG. 1, an image selection unit 107 receives an image selection designation issued by the operator. The image selection unit 107 is configured by an input device such as a mouse or a keyboard. The operator can select an image by operating the image selection unit 107. The operator can designate reshooting of the image selected by the image selection unit 107.

A reshooting designation unit 108 can be operated by the operator to designate reshooting. The reshooting designation unit 108 is similar to the image selection unit 107 in that the reshooting designation unit 108 is configured by an input device such as a mouse or a keyboard. A reason-for-reshooting input unit 109 can be operated by the operator to input a reason for reshooting. The reason-for-reshooting input unit 109 is similar to the image selection unit 107 in that the reason-for-reshooting input unit 109 is configured by an input device such as a mouse or a keyboard. The image selection unit 107, the reshooting designation unit 108, and the reason-for-reshooting input unit 109 can all be set to have the same configuration.

A transition-to-reshooting-state unit 110 puts, into a reshooting state (i.e., a state in which reshooting is designated), a photographed image acquired by the photographed image acquisition unit 102. A photographed image to be put by the transition-to-reshooting-state unit 110 into the reshooting state is determined based on information input to the image selection unit 107, the reshooting designation unit 108, or the reason-for-reshooting input unit 109. However, it is determined by a control unit 111 which of images is put in the reshooting state.

The control unit 111 has a configuration similar to that of a general personal computer, and to that of the combined image generation unit 104. The control unit 111 functions as a setting unit. When the reshooting designation unit 108 issues a reshooting designation with respect to the selected image, the control unit 111 determines whether the selected image is a target of reshooting. Then, the control unit 111 causes the transition-to-reshooting-state unit 110 to put, into the reshooting state, the image determined as the target of reshooting.

More specifically, when the reshooting designation unit 108 designates reshooting, the control unit 111 determines which of the ordinary shooting mode and the stitch shooting mode the shooting mode currently selected by the shooting mode selection unit 106 is. If the control unit 111 determines that the currently selected shooting mode is the ordinary shooting mode, the control unit 111 instructs the transition-to-reshooting-state unit 110 to put only the image selected by the image selection unit 107 into the reshooting state. On the other hand, if the control unit 111 determines that the currently selected shooting mode is the stitch shooting mode, the control unit 111 instructs the transition-to-reshooting-state unit 110 to put, into the reshooting state, all of the photographed images photographed in the stitch shooting mode and a combined image generated from the photographed images. Thus, the transition to the reshooting state can be changed according to the shooting mode. In the stitch shooting mode, all of the photographed images and the combined image are interlocked for the transition to the reshooting state.

When the current shooting mode is the ordinary shooting mode, the control unit 111 applies the reason for reshooting input by the reason-for-reshooting input unit 109 only to an image selected by the image selection unit 107. On the other hand, when the current shooting mode is the stitch shooting mode, the control unit 111 applies the reason for reshooting input by the reason-for-reshooting input unit 109 to all of the images photographed in the stitch shooting mode and the combined image generated from the photographed images. Consequently, the application of the reason for reshooting in the stitch shooting mode to each of the photographed images and the combined image generated from the photographed images is performed in an interlocking manner.

Figure 3:
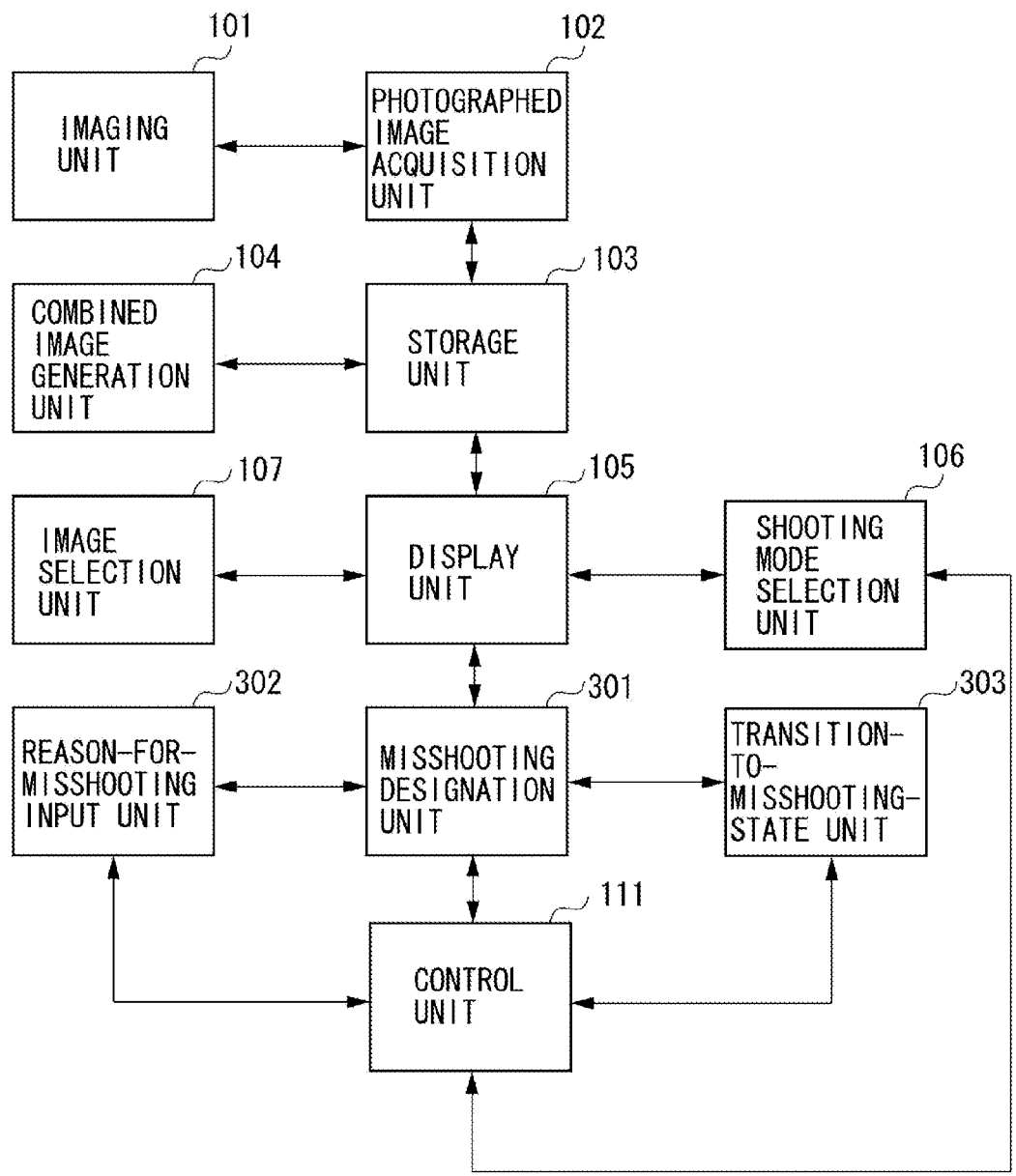
FIG. 3 illustrates a configuration of an image processing apparatus differing in configuration from the image processing apparatus illustrated in FIG. 1.

FIG. 3 illustrates a configuration of an image processing apparatus differing in configuration from the image processing apparatus illustrated in FIG. 1. The components of the image processing apparatus illustrated in FIG. 3 other than the following units 301, 302, and 303 are similar to those illustrated in FIG. 1. Therefore, the description of such components is not repeated here.

A misshooting designation unit 301 can be operated according to the designation of the operator thereof to designate misshooting of a photographed image. A reason-for-misshooting input unit 302 can be operated according to the designation of the operator to input to the image processing apparatus a reason for misshooting of a photographed image. Each of the misshooting designation unit 301 and the reason-for-misshooting input unit 302 is configured by an input device, such as a mouse or a keyboard, for receiving a designation from the operator. A transition-to-misshooting-state unit 303 puts the photographed images and the combined image generated from the photographed images into a misshooting state in which the misshooting is designated.

An operator's image selection instruction to select one of the photographed images and the combined image generated therefrom is implemented by the image selection unit 107. The operator can designate misshooting of an image selected by the image selection unit 107. The designation of misshooting is implemented by the misshooting designation unit 301.

When the image is put in the misshooting state, the input of a reason for misshooting is implemented by the reason-for-misshooting input unit 302.

When the misshooting designation unit 301 designates misshooting of the selected image, the transition-to-misshooting-state unit 303 put the selected image into the misshooting state. The image to be put in the misshooting state is determined by the control unit 111. More specifically, when the misshooting designation unit 301 designates misshooting, the control unit 111 determines which of the ordinary shooting mode and the stitch shooting mode the current shooting mode selected by the shooting mode selection unit 106 is. If the control unit 111 determines that the current shooting mode is the ordinary shooting mode, the control unit 111 instructs the transition-to-misshooting-state unit 303 to put, into the misshooting state, only the image selected by the image selection unit 107. On the other hand, if the control unit 111 determines that the current shooting mode is the stitch shooting mode, the control unit 111 instructs the transition-to-misshooting-state unit 303 to put, into the misshooting state, all of the images photographed in the stitch shooting mode and the combined image generated therefrom. Consequently, the transition of the image to the misshooting state can be changed according to the shooting mode. In the stitch shooting mode, all of the photographed images and the combined image can be interlocked for the transition to the misshooting state.

When the current shooting mode is the ordinary shooting mode, the control unit 111 applies the reason for reshooting input by the reason-for-reshooting input unit 109 only to the image selected by the image selection unit 107. On the other hand, when the current shooting mode is the stitch shooting mode, the control unit 111 applies the reason for reshooting input by the reason-for-reshooting input unit 109 to all of the images photographed in the stitch shooting mode and the combined image generated from the photographed images. Consequently, the application of the reason for reshooting in the stitch shooting mode to each of the photographed images and the combined image generated from the photographed images is performed in an interlocking manner.

Next, a specific process in the case of performing the designation of misshooting or reshooting with the above configuration is described hereinafter.

Figure 4:
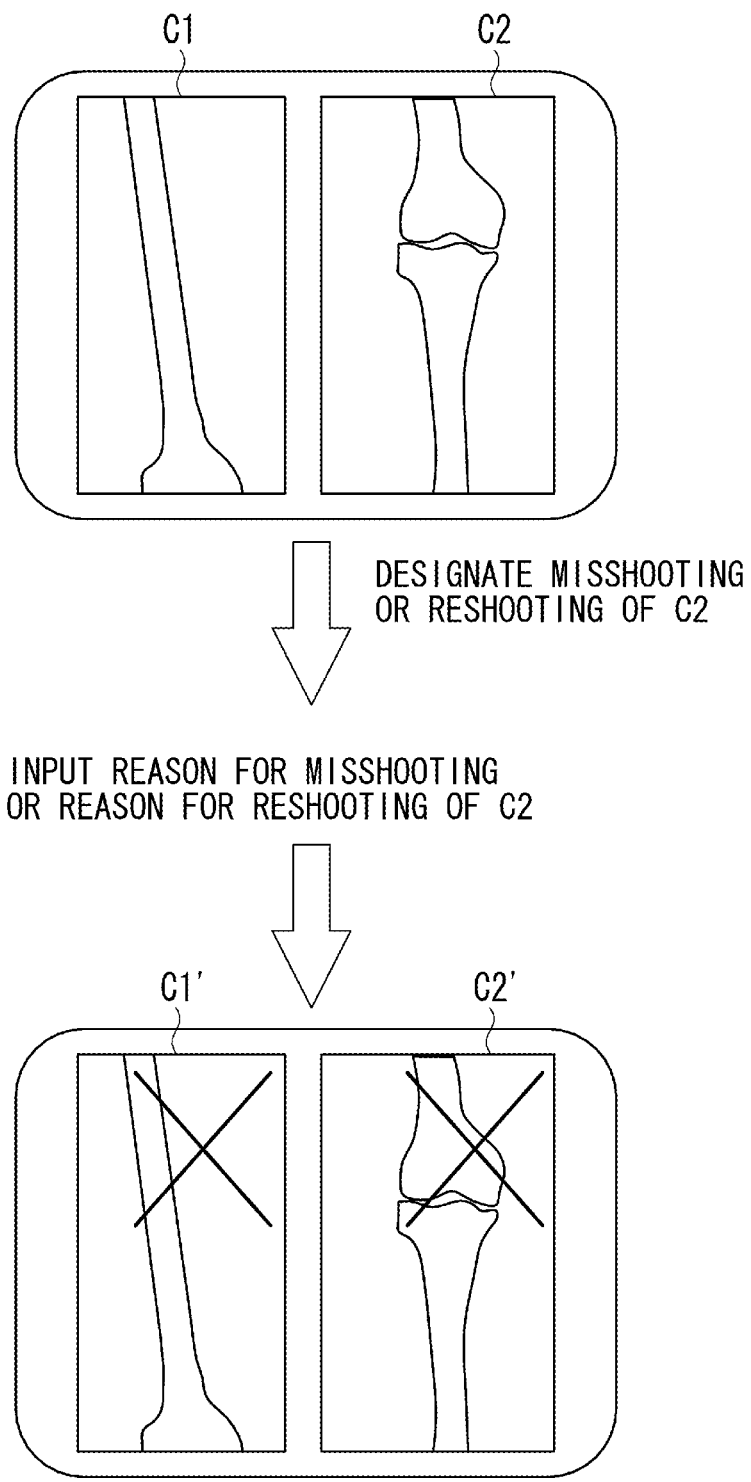
FIG. 4 illustrates a process in the case of designation of misshooting or reshooting of a photographed image.

FIG. 4 illustrates such a process in a case where two images are photographed in the stitch shooting mode, the second one of the photographed images is not obtained as a desired image, and the misshooting or reshooting of the second one of the photographed images is designated.

Figure 9A:
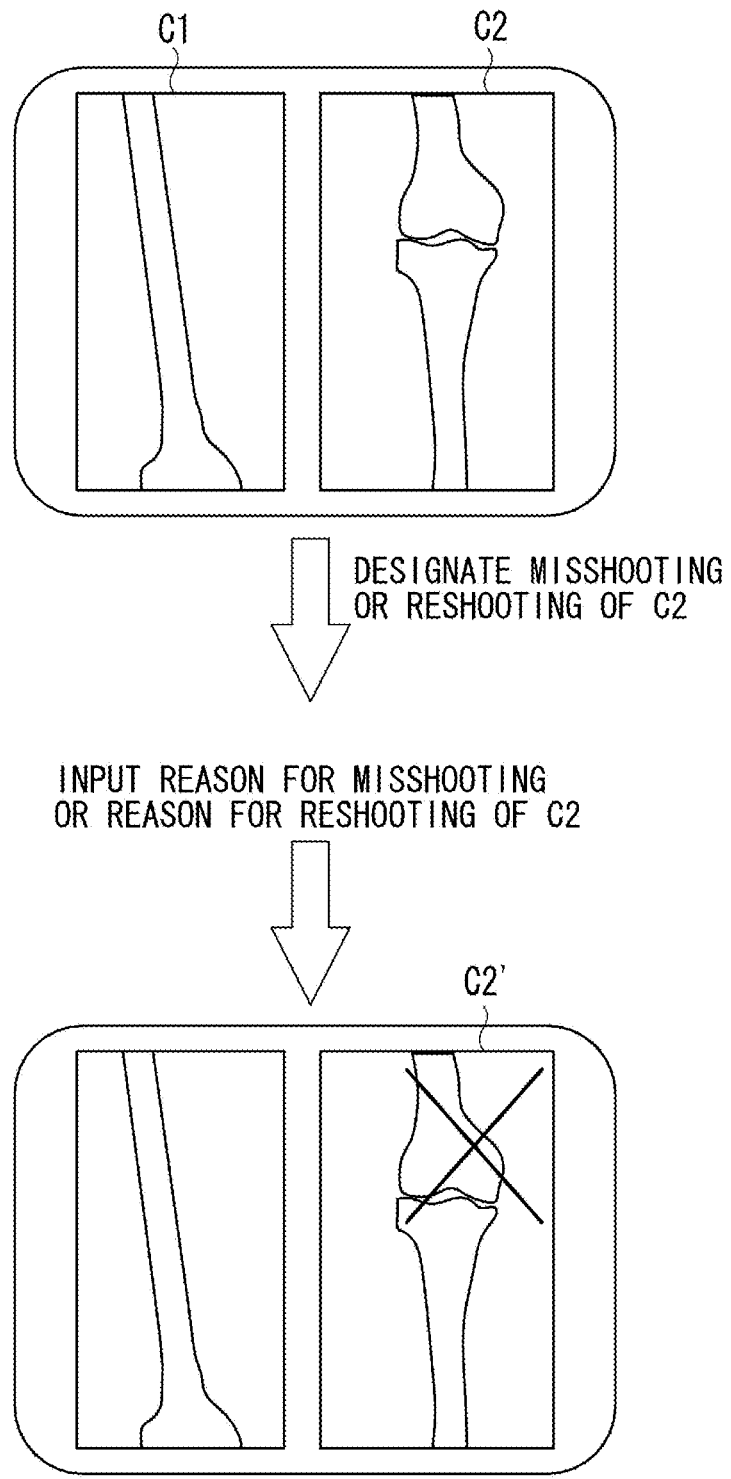
FIGS. 9A and 9B illustrate a conventional method for designation of misshooting or reshooting.
Figure 9B:
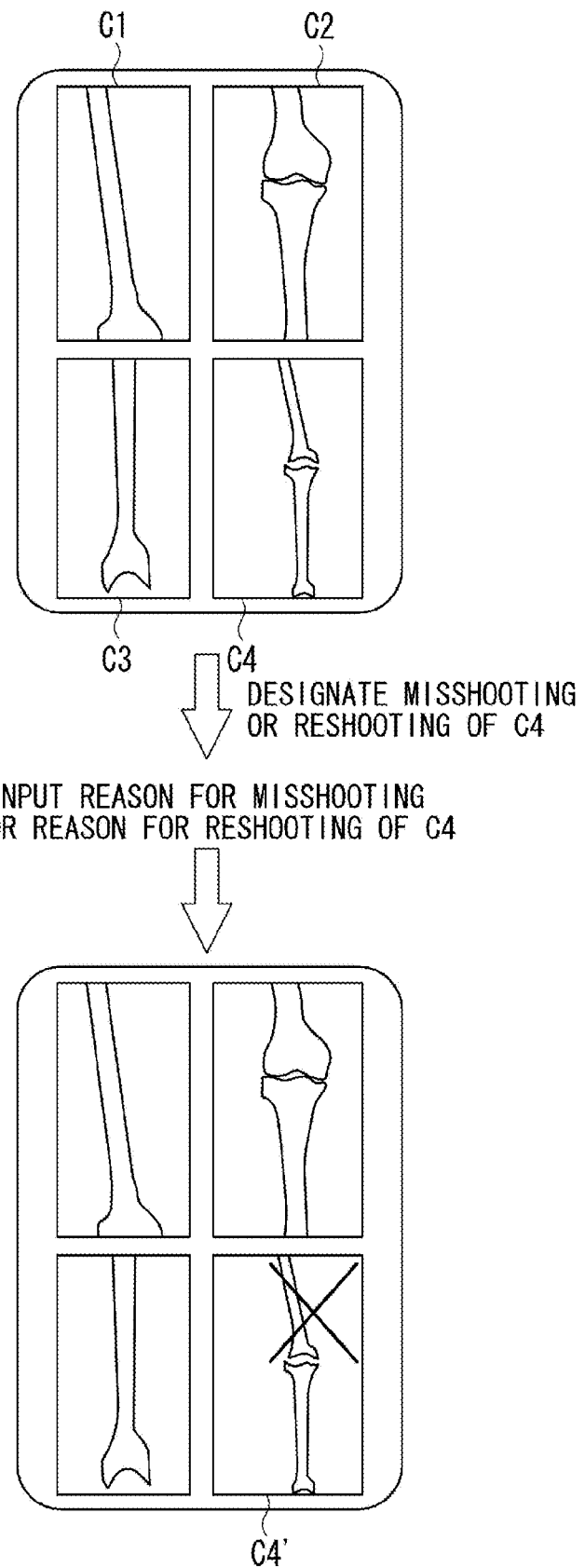

The operator designates the misshooting or reshooting of the photographed image C2, similarly to the case of the conventional method described with reference to FIG. 9A. This operation is performed by the misshooting designation unit 301 or the reshooting designation unit 108. When the misshooting designation unit 301 (or the reshooting designation unit 108) designates misshooting (or reshooting) of the photographed image C2, a screen for inputting a reason for misshooting or reshooting is displayed on the display unit 105. The operator inputs, in the displayed screen, the reason for misshooting or reshooting. The input is performed through the reason-for-misshooting input unit 302 or the reason-for-reshooting input unit 109. The above interactive processing between the operator and the image processing apparatus is performed by the control unit 111 controlling each component thereof according to the present exemplary embodiment.

Upon completion of inputting the reason for misshooting or reshooting, the transition to the misshooting state or the reshooting state is performed by the transition-to-misshooting-state unit 303 or the transition-to-reshooting-state unit 110. At that time, the control unit 1110 determines the current shooting mode. In the process illustrated in FIG. 4, the current shooting mode is the stitch shooting mode. Thus, the control unit 111 instructs the transition-to-misshooting-state unit 303 or the transition-to-reshooting-state unit 110 to put both of the photographed images C1 and C2 into the misshooting state or the reshooting state. Then, the transition-to-misshooting-state unit 303 or the transition-to-reshooting-state unit 110 puts, based on the instruction from the control unit 111, the photographed images C1 and C2 into the misshooting state or the reshooting state. In addition, cross marks are displayed on the photographed images C1 and C2, respectively. Thus, the photographed images C1 and C2 are changed to images C1' and C2', respectively.

Because the current shooting mode is the stitch shooting mode, the control unit 111 applies the reason for misshooting or that for reshooting input from the reason-for-misshooting input unit 302 or the reason-for-reshooting input unit 109 to both of the photographed images C1 and C2.

Thus, in the stitch shooting mode, the misshooting or reshooting of each of the images is implemented in an interlocking manner. Consequently, as compared with a process of sequentially designating the misshooting or reshooting of each of the images in the stitch shooting mode, the process according to the present exemplary embodiment can reduce burden imposed on operators.

The designation of misshooting or reshooting of the photographed image C2 has been described with reference to FIG. 4. However, the designation of misshooting or reshooting is not always performed with respect to the photographed image C2. Even if the designation of misshooting or reshooting is performed with respect to the photographed image C1, similar processing is performed.

FIG. 5 illustrates such a process in a case where photographing of each of images C1, C2, and C3 is finished in the stitch shooting mode, although a combined image C4 is generated, a desired image is not obtained as the combined image C4, and the misshooting or reshooting of the photographed image C2 is designated.

An operator designates misshooting or reshooting of the photographed image C2. This designation is performed by the misshooting designation unit 301 or the reshooting designation unit 108. When the misshooting or reshooting is designated by the misshooting designation unit 301 or the reshooting designation unit 108, a screen for inputting a reason for misshooting or reshooting is displayed on the display unit 105. The operator inputs, in the displayed screen, the reason for misshooting or reshooting. The input is performed through the reason-for-misshooting input unit 302 or the reason-for-reshooting input unit 109.

Upon completion of inputting the reason for misshooting or reshooting, the transition to the misshooting state or the reshooting state is performed by the transition-to-misshooting-state unit 303 or the transition-to-reshooting-state unit 110. At that time, the control unit 111 determines the current shooting mode. In the exemplary embodiment illustrated in FIG. 5, the current shooting mode is the stitch shooting mode. Thus, the control unit 111 instructs the transition-to-misshooting-state unit 303 or the transition-to-reshooting-state unit 110 to put all of the photographed images C1, C2, and C3 and the combined image C4 into the misshooting state or the reshooting state. Then, the transition-to-misshooting-state unit 303 or the transition-to-reshooting-state unit 110 puts, based on the instruction from the control unit 111, the photographed images C1, C2, and C3 and the combined image C4 into the misshooting state or the reshooting state. In addition, cross marks are displayed on the photographed images C1, C2, and C3 and the combined image C4, respectively. Thus, the photographed images C1, C2, and C3 and the combined image C4 are changed to images C1', C2', C3' and C4', respectively.

Because the current shooting mode is the stitch shooting mode, the control unit 111 applies the reason for misshooting or that for reshooting input from the reason-for-misshooting input unit 302 or the reason-for-reshooting input unit 109 to all of the photographed images C1, C2, and C3 and the combined image C4.

Thus, in the stitch shooting mode, the misshooting or reshooting of the images is implemented in an interlocking manner. Consequently, as compared with a process of sequentially designating the misshooting or reshooting of each of the images in the stitch shooting mode, the process according to the present exemplary embodiment can reduce burden imposed on operators.

The designation of misshooting or reshooting of the photographed image C2 has been described with reference to FIG. 5. However, the designation of misshooting or reshooting is not always performed with respect to the photographed image C2. Even if the designation of misshooting or reshooting is performed with respect to the photographed image C1 or C3 or the combined image C4, similar processing is performed.

Figure 6:
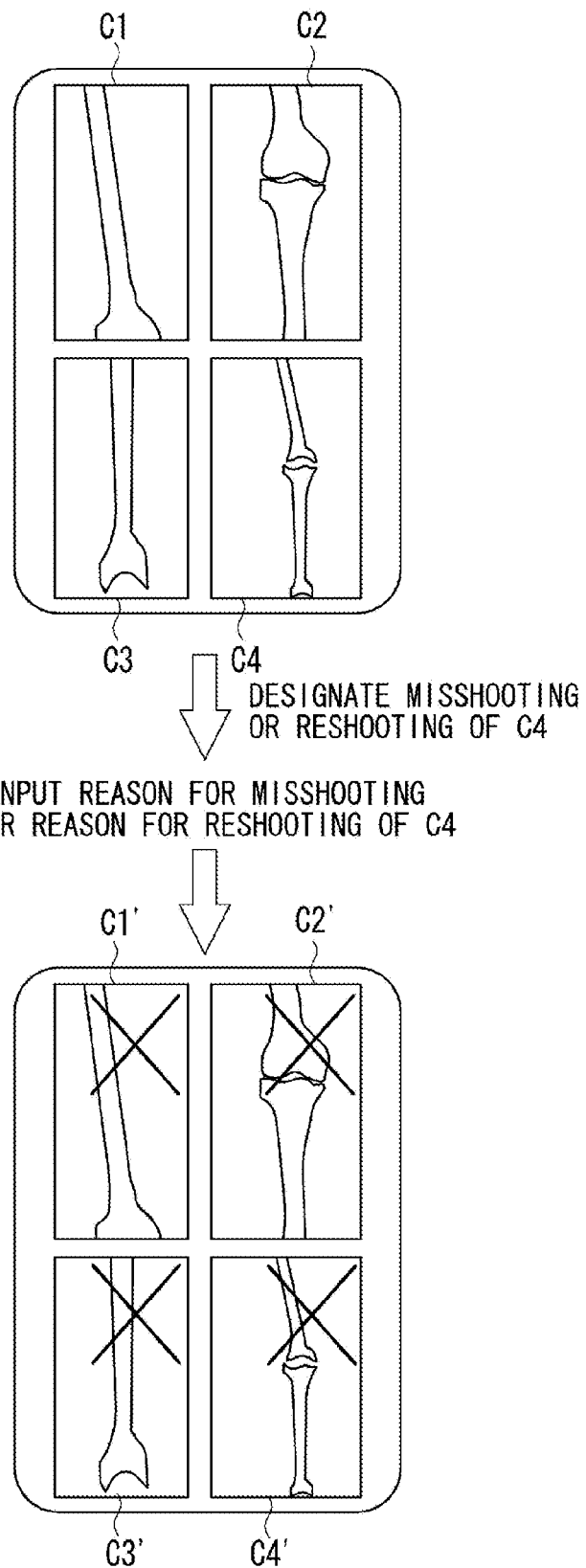
FIG. 6 illustrates another process in the case of designation of misshooting or reshooting of a combined image.

FIG. 6 illustrates such a process in a case where photographing of each of images C1, C2, and C3 is finished in the stitch shooting mode, although a combined image C4 is generated, a desired image is not obtained as the combined image C4, and the misshooting or reshooting of the combined image C4 is designated.

An operator designates misshooting or reshooting of the combined image C4. This designation is performed by the misshooting designation unit 301 or the reshooting designation unit 108. When the misshooting or reshooting is designated by the misshooting designation unit 301 or the reshooting designation unit 108, a screen for inputting a reason for misshooting or reshooting is displayed. The operator inputs, in the displayed screen, the reason for misshooting or reshooting. The input is performed via the reason-for-misshooting input unit 302 or the reason-for-reshooting input unit 109.

Upon completion of inputting the reason for misshooting or reshooting of the image, the transition to the misshooting state or the reshooting state is performed by the transition-to-misshooting-state unit 303 or the transition-to-reshooting-state unit 110. At that time, the control unit 111 determines the current shooting mode. In the exemplary embodiment illustrated in FIG. 6, the current shooting mode is the stitch shooting mode. Thus, the control unit 111 instructs the transition-to-misshooting-state unit 303 or the transition-to-reshooting-state unit 110 to put all of the photographed images C1, C2, and C3 and the combined image C4 into the misshooting state or the reshooting state. Then, the transition-to-misshooting-state unit 303 or the transition-to-reshooting-state unit 110 puts, based on the instruction from the control unit 111, the photographed images C1, C2, and C3 and the combined image C4 into the misshooting state or the reshooting state. In addition, cross marks are displayed on the photographed images C1, C2, and C3 and the combined image C4, respectively. Thus, the photographed images C1, C2, and C3 and the combined image C4 are changed to images C1', C2', C3', and C4', respectively.

Because the current shooting mode is the stitch shooting mode, the control unit 111 applies the reason for misshooting or that for reshooting input from the reason-for-misshooting input unit 302 or the reason-for-reshooting input unit 109 to all of the photographed images C1, C2, and C3 and the combined image C4.

Thus, in the stitch shooting mode, the misshooting or reshooting of each of the images is implemented in an interlocking manner. Consequently, as compared with a process of sequentially designating the misshooting or reshooting of each of the images in the stitch shooting mode, the process according to the present exemplary embodiment can reduce burden imposed on operators.

The designation of misshooting or reshooting of the combined image C4 has been described with reference to FIG. 6. However, the designation of misshooting or reshooting is not always performed with respect to the combined image C4. Even if the designation of misshooting or reshooting is performed with respect to the photographed image C1, C2, or C3, similar processing is performed.

Figure 7:
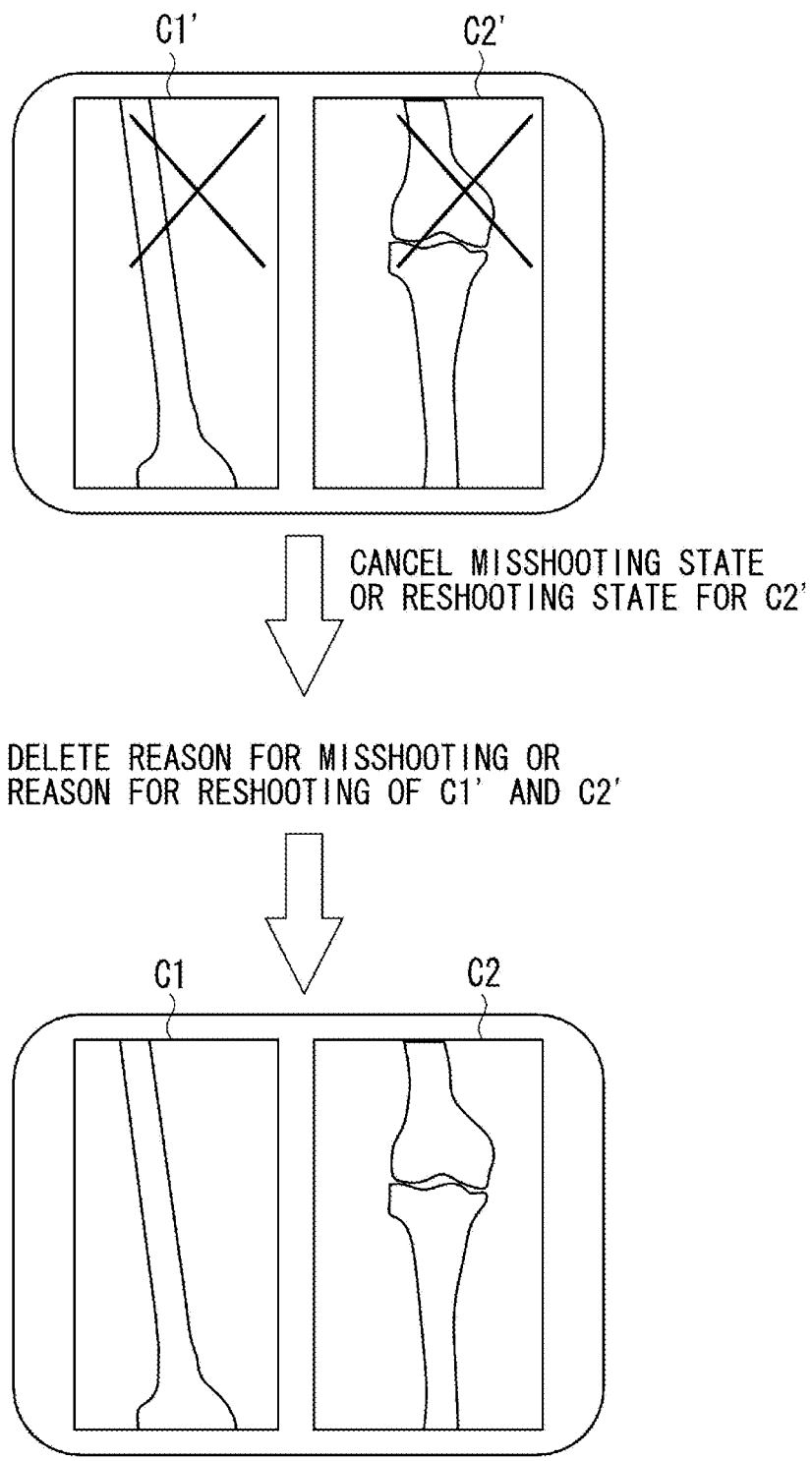
FIG. 7 illustrates a process in the case of cancelling the designation of misshooting or reshooting.

FIG. 7 illustrates a process in a case where after the transition of each of the photographed images C1 and C2 into the misshooting state or the reshooting state, the designation of the misshooting state or the reshooting state is canceled.

An operator instructs the cancellation of the misshooting state or reshooting state of the photographed image C2. This processing is performed by the misshooting designation unit 301 or the reshooting designation unit 108. When the cancellation of the misshooting state or reshooting state is instructed by the misshooting designation unit 301 or the reshooting designation unit 108, the misshooting state or the reshooting state is canceled by the transition-to-misshooting-state unit 303 or the transition-to-reshooting-state unit 110. At that time, the control unit 111 determines the current shooting mode. In the exemplary embodiment illustrated in FIG. 7, the current shooting mode is the stitch shooting mode. Thus, the control unit 111 instructs the transition-to-misshooting-state unit 303 or the transition-to-reshooting-state unit 110 to cancel the misshooting state or the reshooting state of each of the photographed images C1' and C2'. Then, the transition-to-misshooting-state unit 303 or the transition-to-reshooting-state unit 110 cancels, based on the instruction issued by the control unit 111, the misshooting state or the reshooting state of each of the photographed images C1' and C2'. Then, cross marks formed on the photographed images C1' and C2' are deleted. Thus, the photographed images C1' and C2' are changed to images C1 and C2, respectively.

In addition, because the current shooting mode is the stitch shooting mode, the control unit 111 deletes the reason for misshooting or reshooting of each of the input photographed images C1' and C2', which are input by the reason-for-misshooting input unit 302 or the reason-for-reshooting input unit 109.

Thus, in the stitch shooting mode, the misshooting state or reshooting state of each of the images is canceled in an interlocking manner. Consequently, as compared with a process of sequentially canceling the misshooting or reshooting of each of the images in the stitch shooting mode, the process according to the present exemplary embodiment can reduce burden imposed on operators.

The instruction to cancel the misshooting state or the reshooting state of the photographed image C2' has been described with reference to FIG. 7. However, the cancellation of the misshooting state or the reshooting state is not always instructed with respect to the photographed image C2'. Even if the cancellation of the misshooting state or the reshooting state is instructed with respect to the photographed image C1', similar processing is performed.

FIG. 8 illustrates a process of cancelling the designation of misshooting or reshooting after each of the photographed images C1, C2, and C3, and the combined image C4 is put in the misshooting state or the reshooting state by the operation illustrated in FIG. 5 or 6.

An operator issues an instruction to cancel the misshooting state or the reshooting state of the combined image C4'. The issuance of the instruction is performed by the misshooting designation unit 301 or the reshooting designation unit 108. When the instruction to cancel the misshooting state or the reshooting state is issued by the misshooting designation unit 301 or the reshooting designation unit 108, the misshooting state or the reshooting state is canceled by the transition-to-misshooting-state unit 303 or the transition-to-reshooting-state unit 110. At that time, the control unit 111 determines the current shooting mode. In the exemplary embodiment illustrated in FIG. 8, the current shooting mode is the stitch shooting mode. The control unit 111 issues, to the transition-to-misshooting-state unit 303 or the transition-to-reshooting-state unit 110, an instruction to cancel the misshooting state or the reshooting state of each of the images C1', C2', C3', and C4'. Then, the transition-to-misshooting-state unit 303 or the transition-to-reshooting-state unit 110 cancels, based on the instruction from the control unit 111, the misshooting state or the reshooting state of each of the photographed images C1', C2', and C3' and the combined image C4'. In addition, cross marks respectively formed on the photographed images C1', C2', and C3' and the combined image C4' are deleted. Thus, the images C1', C2', C3', and C4' are changed to images C1, C2, C3, and C4, respectively.

Because the current shooting mode is the stitch shooting mode, the control unit 111 deletes the reason for misshooting or reshooting of each of the images C1', C2', C3', and C4' input by the reason-for-misshooting input unit 302 or the reason-for-reshooting input unit 109.

Thus, in the stitch shooting mode, the misshooting state or reshooting state of each of the images is canceled in an interlocking manner. Consequently, the process according to the present exemplary embodiment can reduce burden imposed on operators.

The instruction to cancel the misshooting state or the reshooting state of the combined image C4' has been described with reference to FIG. 8. However, the cancellation of the misshooting state or the reshooting state is not always instructed with respect to the combined image C4'. Even if the cancellation of the misshooting state or the reshooting state is instructed with respect to each of the photographed images C1', C2', and C3', similar processing is performed.

In the above exemplary embodiment, an example of shooting three images has been described. However, the number of images photographed in the stitch shooting mode is not always three. The number of images photographed in the stitch shooting mode may be either two or more than three. The exemplary embodiments of the present invention can be applied to such cases.

Figure 10:
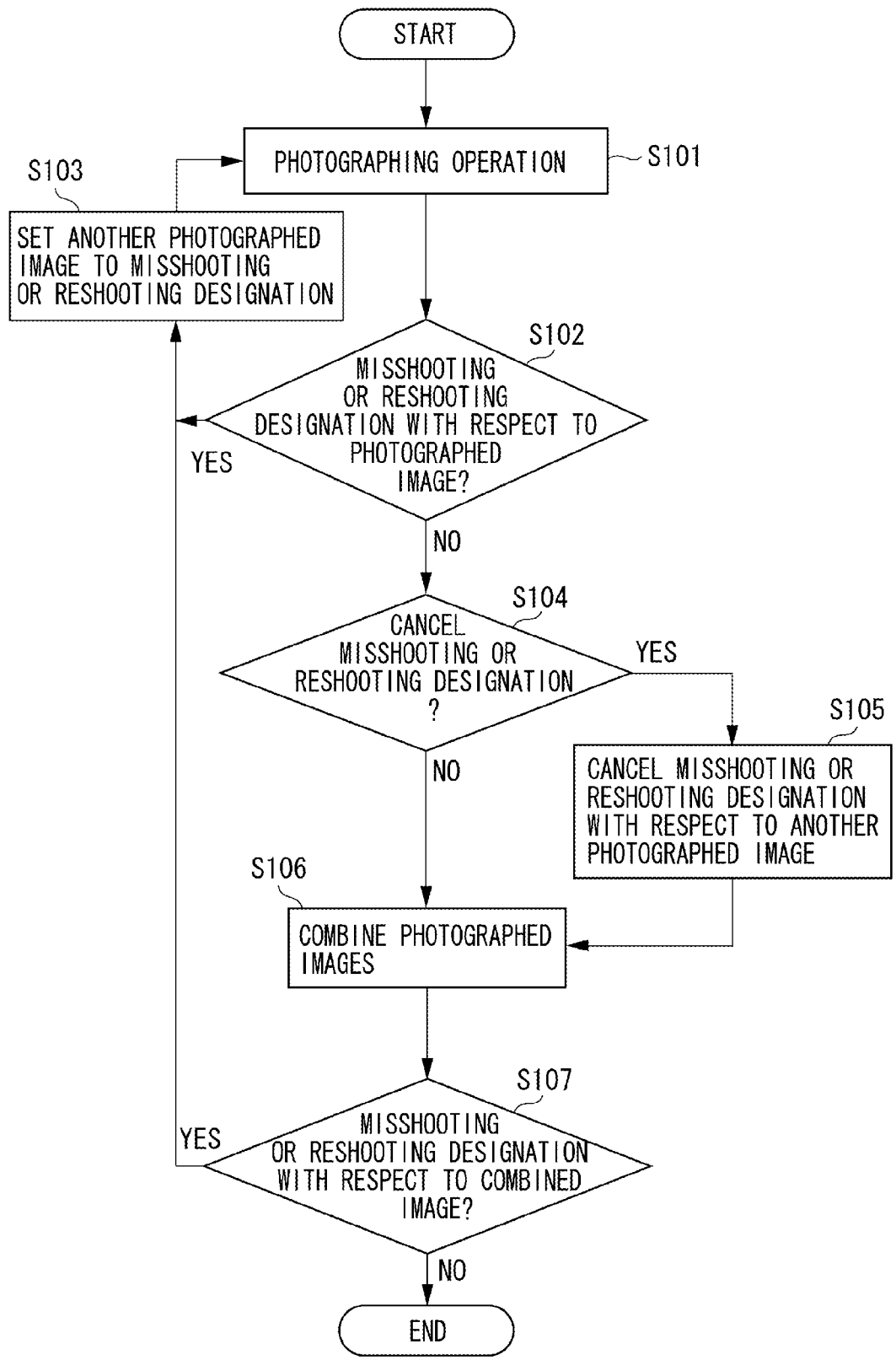
FIG. 10 is a flowchart illustrating processing performed by the image processing apparatus according to an exemplary embodiment of the present invention.

FIG. 10 is a flowchart illustrating processing performed by the image processing apparatus according to the present exemplary embodiment. Processing in steps of the flowchart of FIG. 10 is executed mainly by the control unit 111.

In step S101, the imaging unit 101 photographs an object and, thus, the photographed image acquisition unit 102 acquires a photographed image.

In step S102, the control unit 111 determines whether the misshooting designation unit 301 has issued a misshooting designation or the reshooting designation unit 108 has issued a reshooting designation.

If the misshooting designation unit 301 has issued a misshooting designation or the reshooting designation unit 108 has issued a reshooting designation (YES in step S102), then in step S103, the control unit 111 additionally sets another photographed image, which is a target of stitch shooting, to the misshooting or reshooting designation. The processing then returns to step S101, in which a photographing operation is performed again.

In step S104, the control unit 111 determines whether the operator has issued an instruction for canceling the misshooting or reshooting designation.

If the operator has issued an instruction for canceling the misshooting or reshooting designation (YES in step S104), then in step S105, the control unit 111 additionally cancels the misshooting or reshooting designation with respect to another photographed image, which is a target of stitch shooting.

In step S106, the combined image generation unit 104 combines photographed images to generate a combined image.

In step S107, the control unit 111 determines whether the misshooting designation unit 301 has issued a misshooting designation or the reshooting designation unit 108 has issued a reshooting designation with respect to the combined image.

If the misshooting designation unit 301 has issued a misshooting designation or the reshooting designation unit 108 has issued a reshooting designation with respect to the combined image (YES in step S107), the processing proceeds to step S103. In step S103, the control unit additionally sets another photographed image, which is a target of stitch shooting, to the misshooting or reshooting designation.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-194466 filed Aug. 31, 2010, which is hereby incorporated by reference herein in its entirety.

What is claimed is:

1. An image processing apparatus comprising:
   an imaging unit configured to acquire a plurality of photographed images by detecting radiation;
   a combined image generation unit configured to generate a combined image of at least a first photographed image and a second photographed image among the plurality of photographed images; and
   a setting unit configured to transition the second photographed image of the combined image to a misshooting state or a reshooting state in conjunction with designating a misshooting state or a reshooting state of the first photographed image, if misshooting or reshooting of the first photographed image of the combined image is designated.

2. The image processing apparatus according to claim 1, wherein the combined image generation unit generates the combined image from the first photographed image and the second photographed image, and
   wherein the setting unit transitions the second photographed image and the combined image to the misshooting state or the reshooting state, if the misshooting or reshooting of the first photographed image of the combined image is designated.

3. The image processing apparatus according to claim 1, wherein the combined image generation unit generates the combined image from the first photographed image and the second photographed image, and
   wherein the setting unit transitions the first photographed image and the second photographed image to the misshooting state or the reshooting state, if the misshooting or reshooting of both the first photographed image and the second photographed image of the combined image is designated.

4. The image processing apparatus according to claim 1, further comprising a radiographing unit configured to detect the radiation,
   wherein the plurality of photographed images is a plurality of radiographic images acquired by the radiographing unit detecting the radiation.

5. The image processing apparatus according to claim 4, further comprising a determination unit configured to determine whether the radiographing unit is in a stitch shooting mode or in a single-image shooting mode,
   wherein, if the determination unit determines that the radiographing unit is in the stitch shooting mode and if the misshooting or reshooting of the first photographed image of the plurality of photographed images is designated, the setting unit transitions both the first photographed image and the second photographed image of the combined image to the misshooting state or the reshooting state.

6. The image processing apparatus according to claim 1, further comprising a selection unit configured to select the first photographed image and the second photographed image among the plurality of photographed images to be combined to generate the combined image,
   wherein, if the misshooting or reshooting of the first photographed image is designated, the setting unit transitions the second photographed image of the plurality of the photographed images to the misshooting state or the reshooting state.

7. The image processing apparatus according to claim 1, wherein, if designation of the reshooting or reshooting of the first photographed image is canceled, the setting unit cancels a transition of the second photographed image to the misshooting state or reshooting state.

8. The image processing apparatus according to claim 1, further comprising a
   display unit configured to display the first photographed image and the second photographed image together with the combined image,
   wherein, if the misshooting or reshooting of the first photographed image is designated, the display unit displays a mark on each of the first photographed image, the second photographed image, the combined image, the mark being indicative of the misshooting state or the reshooting state.

9. An image processing method comprising:
   acquiring a plurality of photographed images by using an imaging unit to detect radiation;
   generating a combined image of at least a first photographed image and a second photographed image from among the plurality of photographed images; and
   transitioning the second photographed image of the combined image to a misshooting state or a reshooting state in conjunction with designating the misshooting shooting state or the reshooting stated of the first photographed image, if misshooting or reshooting the first photographed image of the combined image is designated.

10. A non-transitory computer-readable storage medium storing a computer program for causing a computer to perform a method comprising:

acquiring a plurality of photographed images by using an imaging unit to detect radiation;

generating a combined image of at least a first photographed image and a second photographed image from among the plurality of photographed images; and transitioning the second photographed image of the combined image to a misshooting state or a reshooting state in conjunction with designating the misshooting state or reshooting state of the first photographed image, if misshooting or reshooting the first photographed image of the combined image is designated.

11. An image processing apparatus comprising:

an imaging unit configured to acquire a plurality of photographed images by detecting radiation;

a combined image generation unit configured to generate a combined image using the plurality of photographed images; and a setting unit configured to transition all photographed images of the combined image to a misshooting state or a reshooting state in conjunction with designating the misshooting state or the reshooting state of the combined image, if misshooting or reshooting of the combined image is designated.

12. An image processing apparatus comprising:

an imaging unit configured to acquire a plurality of photographed images by detecting radiation;

a selecting unit configured to select an imaging mode among a single-image shooting mode or a stitching shooting mode;

a combined image generation unit configured to generate a combined image by stitching two or more photographed images out of the plurality of photographed images, in a case in where the stitching shooting mode is selected;

a control unit configured to determine whether at least one of the two or more photographed images used to form the combined image requires reshooting; and a setting unit configured set to a misshooting state or a reshooting state of the combined image and the two or more photographed images used to form the combined image, in a case in which at least one of the two or more photographed images used to form the combined image requires reshooting.

* * * * *